(12) United States Patent
Hunt et al.

(10) Patent No.: US 11,426,096 B2
(45) Date of Patent: Aug. 30, 2022

(54) BREATH TESTER

(71) Applicant: Alcolizer Pty Ltd., Brisbane (AU)

(72) Inventors: Roger Alan Hunt, Brisbane (AU); James John Brown, Brisbane (AU)

(73) Assignee: ALCOLIZER PTY LTD, Queensland (AU)

( * ) Notice: Subject to any disclaimer, the term of this patent is extended or adjusted under 35 U.S.C. 154(b) by 950 days.

(21) Appl. No.: 16/301,294

(22) PCT Filed: May 12, 2017

(86) PCT No.: PCT/AU2017/050437
§ 371 (c)(1),
(2) Date: Nov. 13, 2018

(87) PCT Pub. No.: WO2017/193175
PCT Pub. Date: Nov. 16, 2017

(65) Prior Publication Data
US 2020/0315495 A1   Oct. 8, 2020

(30) Foreign Application Priority Data

May 13, 2016   (AU) .............................. 2016901779

(51) Int. Cl.
*A61B 5/097* (2006.01)
*G01N 33/497* (2006.01)
(Continued)

(52) U.S. Cl.
CPC .............. *A61B 5/097* (2013.01); *A61B 5/082* (2013.01); *A61B 5/4845* (2013.01); *A61B 5/742* (2013.01); *G01N 33/497* (2013.01)

(58) Field of Classification Search
CPC .. A61B 5/097; G01N 33/497; G01N 33/4972; G01N 33/98
See application file for complete search history.

(56) References Cited

U.S. PATENT DOCUMENTS 8,466,796 B1 * 6/2013 Mejia ................. G01N 33/4972
340/576
2004/0260194 A1   12/2004 Bayer et al.
(Continued)

FOREIGN PATENT DOCUMENTS

WO         2015117046 A1     8/2015

OTHER PUBLICATIONS

Alcofind AF-100S—How to remove and install the blow cap, Youtube, published Jul. 14, 2015 [retrieved from internet on Sep. 9, 2019] <URL:https://www.youtube.com/watch?v=dQ78tisXHO> 42 pages.

(Continued)

*Primary Examiner* — Herbert K Roberts
(74) *Attorney, Agent, or Firm* — DeLio Peterson & Curcio LLC; Brian G. Schlosser

(57) ABSTRACT

The present invention relates to a breath tester. The breath tester includes a sensor for sensing a mind-altering substance in breath from a blower (i.e., person blowing and providing a sample). A breath guide is provided for guiding the breath so that it is not returned to the blower. Advantageously, the guide guides the breath so that it is not returned to the blower to thereby minimise the likelihood of spread of infectious disease.

16 Claims, 3 Drawing Sheets

(51) Int. Cl.
*A61B 5/08* (2006.01)
*A61B 5/00* (2006.01)

(56) References Cited

U.S. PATENT DOCUMENTS

2012/0157871 A1    6/2012  Walden et al.
2016/0331272 A1*  11/2016  Ahmad .................. A61B 5/082

OTHER PUBLICATIONS

Opposition Correspondence Re-examination 23180549v1-"Request for Re-examination of a Complete Specification" submitted by Dragerwerk AG & Co. KGaA on Jul. 18, 2019, pp. 70-106.

* cited by examiner

BREATH TESTER

TECHNICAL FIELD

The present invention generally relates to a breath tester. The present invention has particular, although not exclusive application to breath testers for testing the presence of mind-altering substances, and alcohol in particular.

BACKGROUND

The reference to any prior art in this specification is not, and should not be taken as an acknowledgement or any form of suggestion that the prior art forms part of the common general knowledge.

Mind-altering substances can impair human performance. Employers can test their employees for mind-altering substances such as alcohol or drugs with a view of ensuring optimum results and compliance in the workplace.

Some workplaces are fitted with wall mounted alcohol breath testers. Workers may be required to pass the test prior to commencing work. In some countries, infectious diseases such as tuberculosis are rife which presents a health risk for workers undertaking testing using the same breath tester.

The preferred embodiment provides an improved breath tester for minimizing the likelihood of spread of infectious disease.

SUMMARY OF THE INVENTION

According to one aspect of the present invention, there is provided a breath tester including:
a sensor for sensing a mind-altering substance, the mind altering substance including alcohol, in breath from a blower; and
a breath guide including:
at least one wall,
an outwardly facing surface for guiding breath from a blower towards the sensor, and
an inwardly facing surface for guiding the breath laterally so that it is not returned directly to the blower;
wherein the inwardly facing surface and the outwardly facing surface form opposing sides of the wall.

The guide guides the breath so that it is not returned to the blower to thereby minimise the likelihood of spread of infectious disease.

The guide may include a breath receptacle for receiving breath from the blower. The receptacle may include a funnel.

The guide may further include breath diversion means for diverting the received breath so that it is not returned to the blower. The breath diversion means may include the funnel. The breath diversion means may further include a well for receiving the guide. The guide may include a wall supporting the funnel. The wall may define one or more apertures through which diverted breath passes.

The breath tester may further include a display for displaying the result of the test. The result may be pass or fail.

According to another aspect of the present invention, there is provided a breath guide for a breath tester, including a sensor for sensing a mind-altering substance, the mind altering substance including alcohol, in breath from a blower the guide including:
a breath receptacle for receiving breath from a blower; and
breath diverter including:
at least one wall,
an outwardly facing surface for guiding breath from a blower towards the sensor, and
an inwardly facing surface for diverting the received breath laterally so that it is not directly returned to the blower;
wherein the inwardly facing surface and the outwardly facing surface form opposing sides of the wall.

Any of the features described herein can be combined in any combination with any one or more of the other features described herein within the scope of the invention.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
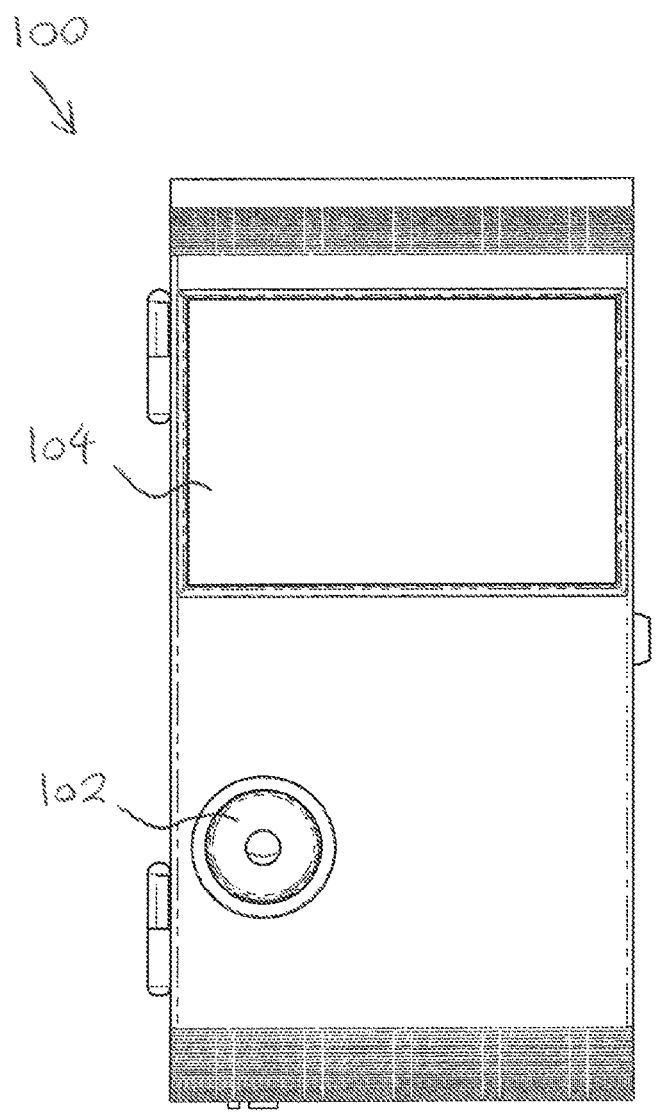
FIG. 1 is a front view of a breath tester in accordance with an embodiment of the present invention.

According to an embodiment of the present invention, there is provided an alcohol breath tester 100 as shown in FIG. 1. The breath tester 100 includes a breath guide 102 for guiding breath so that it is not returned to a blower (i.e., person blowing) undertaking a test. The blower blows into the guide from a distance of about 10 cm and for about 2 seconds. In guiding the breath so that it is not returned to the blower, the guide 102 minimises the likelihood of spread of infectious disease.

Figure 2:
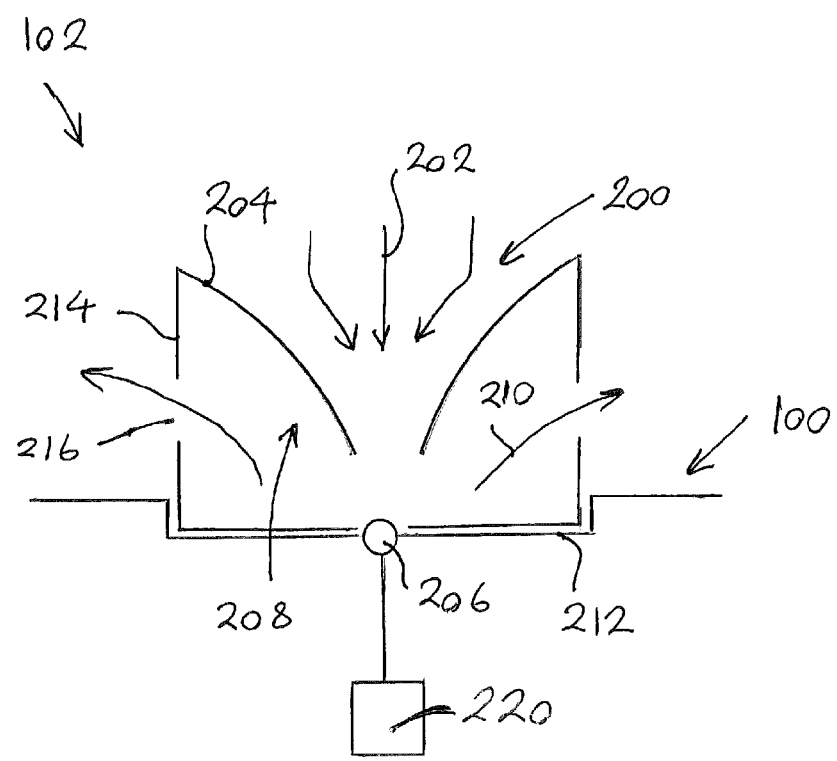
FIG. 2 is a schematic view of the breath tester of FIG. 1.

Turning to FIG. 2, the breath guide 102 includes a breath receptacle 200 for receiving breath 202 from the blower. The receptacle 200 includes a funnel 204 for funneling the breath 202 toward a sensor 206 in register with the funnel 204. The sensor 206 senses a mind-altering substance in the breath 202.

The guide 102 further includes breath diversion means 208 for diverting the received breath 210, after sensing, so that it is not returned to the blower. The breath diversion means 208 includes the underside of the funnel 204, and a well 212 in the face of the tester 100 which receives the guide 102.

Figure 3:
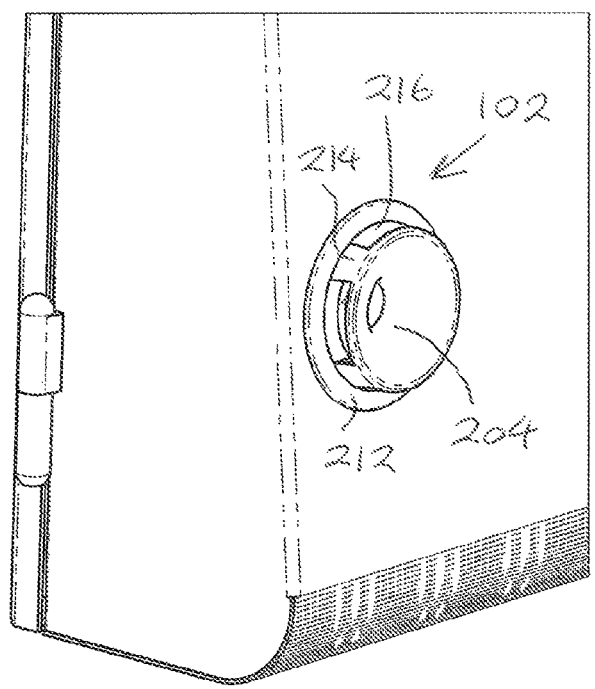
FIG. 3 is a perspective view of a breath guide of the breath tester of FIG. 1.

As can best be seen in FIGS. 2 and 3, the guide 102 further includes a side wall 214 supporting the funnel 204. The wall 214 defines apertures 216 through which diverted breath 210 passes out to the side and not back to the blower. In this regard, the guide 102 provides tremendous benefit whereby if it was not present, blown air would simply be returned from the well 212 to the blower along with mucous from previous blowers that may be carrying infectious disease.

As can best be seen in FIG. 2, the breath tester 100 includes an analyser 220 for analyzing the sensed breath and determining a test result. The analyser 220 need only detect the presence of alcohol for a fail, and issues either a passive pass or fail result. There is no need for pressure sensors or flow rate monitors which are otherwise required to sense the degree of failure (i.e., blood alcohol content).

As can best be seen in FIG. 1, the breath tester 100 includes a display 104 for displaying the result of the test.

A person skilled in the art will appreciate that many embodiments and variations can be made without departing from the ambit of the present invention.

In compliance with the statute, the invention has been described in language more or less specific to structural or methodical features. It is to be understood that the invention is not limited to specific features shown or described since the means herein described comprises preferred forms of putting the invention into effect.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The invention claimed is:

1. A breath tester including:
   a sensor for sensing a mind-altering substance, the mind altering substance including alcohol, in breath from a blower; and
   a breath guide for guiding the breath, the breath guide including:
      a breath receptacle for receiving breath from the blower, including a funnel for funneling the breath towards the sensor;
      a wall supporting the funnel and defining one or more apertures; and
      a breath diverter including the underside of the funnel, arranged to divert the breath through the one or more apertures so that it is not returned directly to the blower.

2. A breath tester as claimed in claim 1, wherein the guide guides the breath to prevent the breath from returning back towards the blower to thereby minimise the likelihood of spread of infectious disease.

3. A breath tester as claimed in claim 1, further including a well for receiving the guide, the well including: a base wall defined by a perimeter, and at least one side wall extending from the base wall, the at least one side wall or walls fully extending around the perimeter of the base wall.

4. A breath tester as claimed in claim 1, further including a display for displaying the result of the test.

5. A breath tester as claimed in claim 4, wherein the result is a pass or fail.

6. A breath tester as claimed in claim 1, wherein the funnel is arcuate.

7. A breath tester as claimed in claim 1, wherein the wall is cylindrical.

8. A breath tester as claimed in claim 1, wherein the sensor is in register with the funnel.

9. A breath tester as claimed in claim 2, wherein the funnel is arcuate.

10. A breath tester as claimed in claim 3, wherein the funnel is arcuate.

11. A breath tester as claimed in claim 4, wherein the funnel is arcuate.

12. A breath guide for a breath tester including a sensor for sensing a mind-altering substance, the mind altering substance including alcohol, in breath from a blower, the breath guide including:
   a breath receptacle for receiving breath from a blower, including a funnel for funneling breath towards the sensor;
   a wall supporting the funnel and defining one or more apertures; and
   a breath diverter including the underside of the funnel and for diverting the received breath laterally through one or more apertures so that it is not directly returned to the blower.

13. A breath guide as claimed in claim 12, wherein the funnel is arcuate.

14. A breath guide as claimed in claim 12, wherein the breath guide is received in a well, the well including: a base wall defined by a perimeter, and at least one side wall extending from the base wall, the at least one side wall or walls fully extending around the perimeter of the base wall.

15. A breath guide as claimed in claim 12, wherein the wall is cylindrical.

16. A breath guide as claimed in claim 12, further including the sensor in register with the funnel.

* * * * *